United States Patent [19]

Starkie

[11] 3,959,494

[45] May 25, 1976

[54] ACTIVE DRIED YEAST COMPOSITION

[75] Inventor: Raymond Denis Starkie, Menstrie, Scotland

[73] Assignee: The Distillers Company (Yeast) Limited, Morden, England

[22] Filed: June 17, 1974

[21] Appl. No.: 480,178

[30] Foreign Application Priority Data

June 22, 1973 United Kingdom............... 29802/73
July 2, 1973 United Kingdom............... 31445/73

[52] U.S. Cl..................................... 426/19; 426/62
[51] Int. Cl.$^2$...................... A21D 2/16; A21D 2/14
[58] Field of Search ................ 426/19, 23, 27, 62; 195/74

[56] References Cited
UNITED STATES PATENTS

| | | | |
|---|---|---|---|
| 2,523,483 | 9/1950 | Stern...................................... | 426/62 |
| 3,615,680 | 10/1971 | Henika et al. ........................ | 426/23 |

FOREIGN PATENTS OR APPLICATIONS

| | | | |
|---|---|---|---|
| 4,516,770 | 7/1970 | Japan.................................... | 426/62 |

*Primary Examiner*—James R. Hoffman
*Attorney, Agent, or Firm*—Lawrence Rosen; E. Janet Berry

[57] ABSTRACT

Storage stable dry compositions containing active dried yeast and edible fat or oil are described. They may also contain flour and optionally other dough forming ingredients and may thus serve as dry compositions to which water can be added to make a dough, for example, for bread making.

13 Claims, No Drawings

ACTIVE DRIED YEAST COMPOSITION

It is well-known to produce baker's yeast in dry particulate form, the resultant baker's yeast being known as "active dried yeast." Such yeast generally has a dry matter content greater than 90% by weight, often 93–96% by weight. Active dried yeast is made by various methods, for example extrusion into pellet form followed by drum drying or by methods which produce powdered materials.

We have surprisingly discovered that a mixture comprising active dried yeast and an edible fat or oil can and generally does have significantly improved stability compared to the active dried yeast alone, i.e., in the absence of the edible fat or oil.

Compositions according to the invention are generally made by forming active dried yeast and then adding the edible fat or oil to it.

The active dried yeast can be pellet yeast, for example, made by drum drying, but preferably it is a powdered active dried yeast, that is to say an active dried yeast having a particle size much smaller than the relatively large pellet particles obtained by drum drying.

One preferred process for making powdered yeast comprises spray drying a liquid yeast composition in air, optionally followed by further drying. For example a liquid yeast containing less than 27 percent dry matter may be sprayed dried to a moisture content of, for example, 40–50 percent dry matter and may then be further dried by, for example, fluidised bed drying. Another preferred method for making powdered yeast comprises comminuting moist yeast, for example, having a dry matter content of 27–40 percent, under conditions of high shear, preferably in air. For example the yeast maybe comminuted while exposed to air, and often while entrained in air, in a mill containing blades that rotate at a speed greater than 2,000 rpm, followed by drying.

Preferably the drying processes are in air, e.g. by passing air through a fluidised bed of yeast or over trays of yeast, the yeast in either instance being surrounded by air throughout the drying process.

A suitable spray drying method is described in British Patent Specification No. 1196786 while suitable comminution methods are described in British Patent Specification No. 1140016 and, now U.S. Pat. No. 3885,049 in British Patent application No. 41144/72 (U.S. Serial No. 342,294 filed Mar. 16, 1973).

The addition of edible fat or oil to preformed active dried yeast, or at least its presence in active dried yeast, results in the yeast being of improved stability even when exposed to air at ambient temperatures for prolonged storage periods, for example two weeks or more. It also has the advantage that the stability of the yeast is so great that flour can be added to the mixture before storage. This is of great value when the yeast is powdered yeast, since it is often not necessary to reconstitute powdered yeast in water in the absence of the flour that is to be used to make the dough. Thus in the invention it is possible to form a composition comprising powdered active dried yeast, edible fat or oil and flour, optionally with other dough forming ingredients, and to form a dough from this merely by mixing in water.

Thus it is now possible to form a ready mix dough composition of satisfactory stability and which comprises all the ingredients necessary in the dough except for water. In such ready mix compositions it is naturally desirable that the proportions of yeast and flour should be such that no additional flour is necessary to make the dough, although further flour can be added if desired.

Various dough forming ingredients maybe included in the compositions.

Salt is one such ingredient. Particularly preferred are ingredients that permit what is now commonly known as "activated dough development," that is to say chemically activated dough development. As is well known 1-cysteine is normally used for bringing about activated dough development and so preferred compositions according to the invention comprise active dried yeast, edible fat or oil, flour and 1-cysteine.

Preferably the compositions additionally contain dough improvers. Suitable commercially available improvers include that sold under the trade name "DYNAREX" marketed by the British Arkady Company Limited. Preferably the compositions contain azodicarbonamide as improver.

Preferred compositions contain from 10 to 100, and most preferably 20 to 60 and most usually 40, parts per million 1-cysteine based on the weight of flour, and from 10 to 100, preferably 20 to 60 and most preferably 30, parts per million azodicarbonamide.

As a result of including the specified activating ingredients in the ready mix dough composition of the invention it is possible to form a dough that is ready for baking within a very short time merely by mixing water into the composition. Mechanical mixing may be used but we find that very satisfactory results are obtained, especially with the yeasts made in the described manner in a mill, for example by the method described in British Patent Specification N0. 1,140,016 or in British Patent application N0. 41144/72 (U.S. Ser. No. 342,294 filed Mar. 16, 1973 ), if hand mixing is used. Thus as a result of the invention the housewife can purchase a dried mix that does not have to be packaged in nitrogen and which is stable and she can merely hand mix water into this and bake the resultant dough a short while, for example half an hour to an hour, after the water is added.

The flour used in compositions of the invention generally has a moisture content of from 8 to 15 percent.

The fat or oil used in the compositions of the invention will usually be one that is a permitted additive in bread. It is particularly common to include in bread ground nut oil and/or a bread fat, for example a bread fat having a slip point of 75°–125°F but preferably below 100°F and so these are preferred. Other fats and oils that may be used include any natural or hardened animal or vegetable oil or fat. Also suitable for use are fatty acid esters, especially glyceryl monostearate. Mixtures of the above materials may also be used.

The proportion of yeast dry matter content: edible fat or oil is generally from 1:4 to 10:1, more preferably 1:1 to 5:1, most preferably from 2:1 to 4:1.

The edible fat or oil may most advantageously be combined with preformed active dried yeast by simple mixing, for example, by hand-stirring or simple mechanical mixing. The fat is usually heated to near its slip point before this blending takes place. When flour and other additives are to be included in the mixture they should be added to a composition of the active dried yeast and the oil or fat as otherwise satisfactory intimate contact between the yeast and the oil or fat may not be easily achieved.

The mixtures of the invention may be stored for prolonged periods in packages that may be sealed or open. In particular they may be stored at ambient temperatures in the presence of air for prolonged periods, for example, for more than a month and often for more than three months.

The following are some examples of the invention. In each of Examples 1 to 6 the active dried yeast was a powdered product made by the method described in British Patent application No. 41144/72 (U.S. Ser. No. 342,294 filed Mar. 16, 1973), namely by comminution of moist yeast, having a dry matter content of about 30 percent, in a mill having rapidly rotating blades and through which air is passed, followed by drying, for example, in a fluidised bed drier, to a dry matter content of 92–96 percent.

EXAMPLE 1

Active dried yeast was treated by thorough hand-mixing with a commercial ground nut oil in the ratio of 4 parts yeast to one part oil by weight. 14.25 grams of this mixture was then blended with 2½lbs. of normal commercially available bread flour, together with 12.1 grams of Dynarex (a commercially available improver) and 20.25 grams salt. As a control 11.4 grams of untreated yeast was made up in a similar flour mixture, thus giving the same quantity of yeast per 2½lbs. flour as in the experimental example.

The yeast/flour mixtures were then stored at ambient temperature (70°/75°F) for 14 days in an atmosphere of air. The proof times of this mix were then determined following the addition of 650 mls. of water and mixing in a Morton/Duplex machine for sufficient time to give a work input of 5 watt hours per pound of dough. With a dough temperature of 32.2°C an intermediate proof time of 15 mins. was given. Thereafter a final proof of 35°C to a height of 15 centimeters was given.

The final proof time for the yeast/flour mixture where the yeast had been treated with ground nut oil was 68 mins. compared with a much longer proof time of 81 mins. for the non-treated yeast.

EXAMPLE 2

Example 1 was repeated, excepting that the ground nut oil treated yeast was treated in the ratio of yeast to oil of 2 to 1, and 17.1 grams of this mixture was taken to 2.5lbs. of flour. On final proof times, it was found that the oil treated yeast/flour mixture had a proof time of 60 mins. compared with the 81 mins. of the control.

EXAMPLE 3

Examples 1 and 2 were repeated excepting that the storage time before test was 28 days. The control (no oil treatment of the yeast) had a final proof time of 109 mins. The 4 to 1 yeast/oil mixture had a final proof time of 90 mins. and the 2 to 1 yeast/oil mixture had a final proof time of 75 mins.

EXAMPLE 4

A similar series of Examples was carried out substituting bread fat with a slip point of 100°F for ground nut oil. Active dried yeast was treated with this fat by heating the fat to 80°F and blending with the yeast at the rate of 2 parts yeast 1 part fat by weight. 17.1 grams of this mixture was taken to 2.5lbs. of flour in preparing the mix.

The non-treated yeast/flour mix had a proof time of 90 mins. The mixture where the yeast had been treated with fat had a proof time of only 71 mins.

EXAMPLE 5

Example 4 was repeated, excepting that a different sample of yeast was used throughout. Final proof time of the non-treated yeast/flour mixture was 106 mins. whereas that treated with fat had a proof time of only 68 mins.

Similar relative improvements have been observed during storage over much longer periods, e.g. 10 weeks.

Similar relative improvements have been observed when mixtures of the active dried yeast and the fat or oil have been stored in the absence of flour and then reconstituted in water before use.

EXAMPLE 6

Yeast was blended with ground nut oil in the manner described in Example 2 and 20 grams of the product were mixed with 2 lbs. 8ozs of Democrat flour marketed by R.H.M. Mills Limited, 20.25 grams salt, 8 grams high melting fat, 12.1 grams soya flour, 40 parts per million based on the weight of flour 1-cysteine and 30 parts per million based on the weight of flour of azodicarbonamide.

The resultant dry mix, which could be stored under ambient conditions, was then mixed with 660 ml water by hand mixing. The resultant product had a very satisfactory proof time.

Very satisfactory results were also obtained when hard fat was used instead of the groundnut oil.

EXAMPLE 7

Four parts by weight dried matter of drum dried active dried pellet yeast and one part by weight of groundnut oil were thoroughly mixed together. The treated pellet yeast was then re-hydrated for 15 mins in 100 mls water at 100°F. 14.25 grams dry weight of the resultant mixture was then blended with 2½lbs of normal commercially available bread flour, together with 12.1 grams of DYNAREX and 20.25 grams salt and 550 mls water, bringing the total volume of water to 650 mls. This was mixed as in Example 1 and gave a proof time of 49 minutes. In a control experiment, conducted in the same manner except that no groundnut oil had been included with the yeast, the proof time was 54 minutes. In another experiment the re-hydration was at 80°F, which is a low temperature but is advantageous in areas of high ambient temperature where higher reconstitution temperatures lead to excessively high dough temperatures, a proof time of 60 minutes was recorded compared to a proof time of 63 minutes for a control containing no groundnut oil.

The processes of this example were also repeated after storing the pellet yeast at 80°F for 16 weeks as an accelerated ageing test. When re-hydration was at 100°F the control proof time was 84 minutes while the proof time of the product of the invention was 70 minutes. When re-hydration was at 80°F the control proof time was 106 minutes while the proof time of the product of the invention was 79 minutes.

We claim:
1. A storage stable dry composition from which dough can be formed by merely mixing with water and comprising a dry mixture of (a) flour and (b) mixture formed by intimately mixing predried active dried pow- dered yeast and edible fat or oil in which the proportion by weight of yeast dry matter content to edible fat or oil is from 1:4 to 10:1.

2. A composition according to claim 1 in which the proportion is from 1:1 to 5:1.

3. A composition according to claim 2 in which the proportion is from 2:1 to 4:1.

4. a composition according to claim 1 in which the oil is commerical ground nut oil.

5. A composition according to claim 1 in which the fat has a slip point of below 100°F.

6. A composition according to claim 1 in which the powdered yeast has been produced by comminuting moist yeast in air under high shear followed by drying in air.

7. A composition according to claim 1 in which the powdered yeast has been produced by a process comprising spray drying yeast cream.

8. A composition according to claim 1 additionally comprising 1-cysteine.

9. A composition according to claim 1 additionally including a dough improver.

10. A composition according to claim 9 in which the improver comprises azodicarbonamide.

11. A composition according to claim 1 additionally containing from 20 to 60 parts per million 1-cysteine and 20 to 60 parts per million azodicarbonamide, the parts per million being based on the weight of flour.

12. A method of making bread comprising adding water to a composition according to claim 1 and baking the product.

13. A composition according to claim 1 in which the fat has a slip point of 75° to 125°F.

* * * * *